United States Patent [19]
Keller et al.

[11] Patent Number: 5,353,354
[45] Date of Patent: Oct. 4, 1994

[54] ACQUISITION AND DISPLAY OF ULTRASONIC IMAGES FROM SEQUENTIALLY ORIENTED IMAGE PLANES

[75] Inventors: Philip Keller, Seattle; Larry J. Augustine, Bothell; Ronald E. Daigle, Redmond, all of Wash.

[73] Assignee: Advanced Technology Laboratories, Inc., Bothell, Wash.

[21] Appl. No.: 795,604

[22] Filed: Nov. 21, 1991

[30] Foreign Application Priority Data

Nov. 22, 1990 [GB] United Kingdom ............. 9025431.9

[51] Int. Cl.⁵ .............................................. G06K 9/00
[52] U.S. Cl. .................................. 382/6; 364/413.23; 382/54
[58] Field of Search .................... 382/6, 54, 58, 59; 73/597; 364/413.25, 413.22, 413.19; 348/163

[56] References Cited

U.S. PATENT DOCUMENTS

| | | | |
|---|---|---|---|
| 4,771,470 | 9/1988 | Geiser et al. | 382/54 |
| 4,868,747 | 9/1989 | Mori et al. | 382/6 |
| 4,887,306 | 12/1989 | Hwang et al. | 382/54 |
| 5,050,226 | 9/1991 | Collet-Billon | 382/54 |
| 5,060,515 | 10/1991 | Kanda et al. | 382/6 |
| 5,065,436 | 11/1991 | Matsumura | 382/6 |
| 5,154,080 | 10/1992 | Hill et al. | 73/597 |

*Primary Examiner*—Joseph Mancuso
*Attorney, Agent, or Firm*—W. Brinton Yorks, Jr.

[57] ABSTRACT

An ultrasonic imaging system is disclosed which produces a sequence of images of planes of a subject including both image and spatial positional information of the image plane. In one embodiment the positional information is developed from a plurality of accelerometers located within a scanhead. The second integrals of the acceleration signals are used to determine positional information of the image plane. In a second embodiment a transmitter transmits a magnetic field and a receiver attached to the scanhead detects the position of the scanhead in relation to the transmitted magnetic field. Spatially related images are displayed by displaying one image plane in the plane of the display and a second image plane projected in relation thereto. Either of the displayed planes may be displayed in outline form, and the outline may be modulated to depict depth.

4 Claims, 4 Drawing Sheets

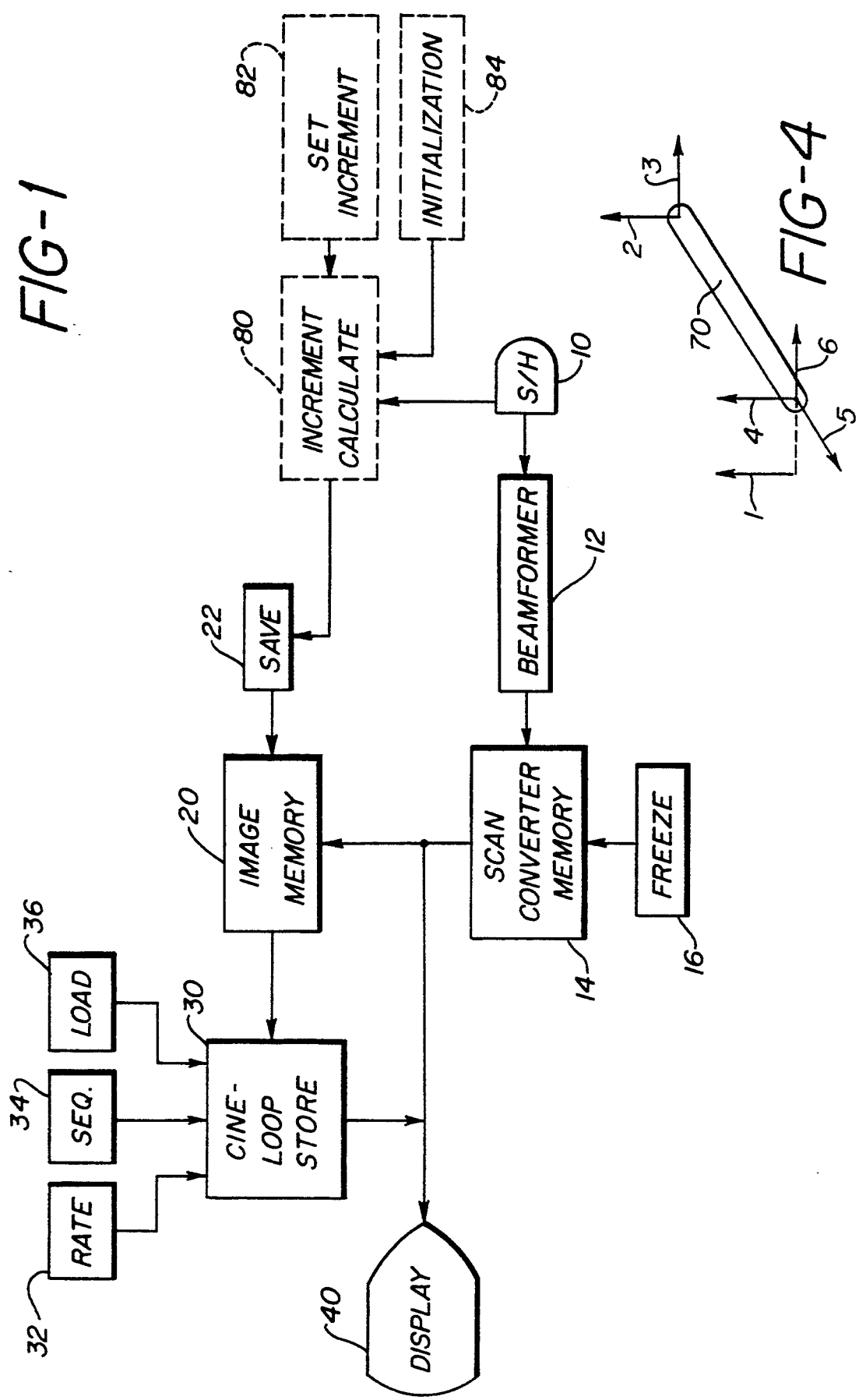

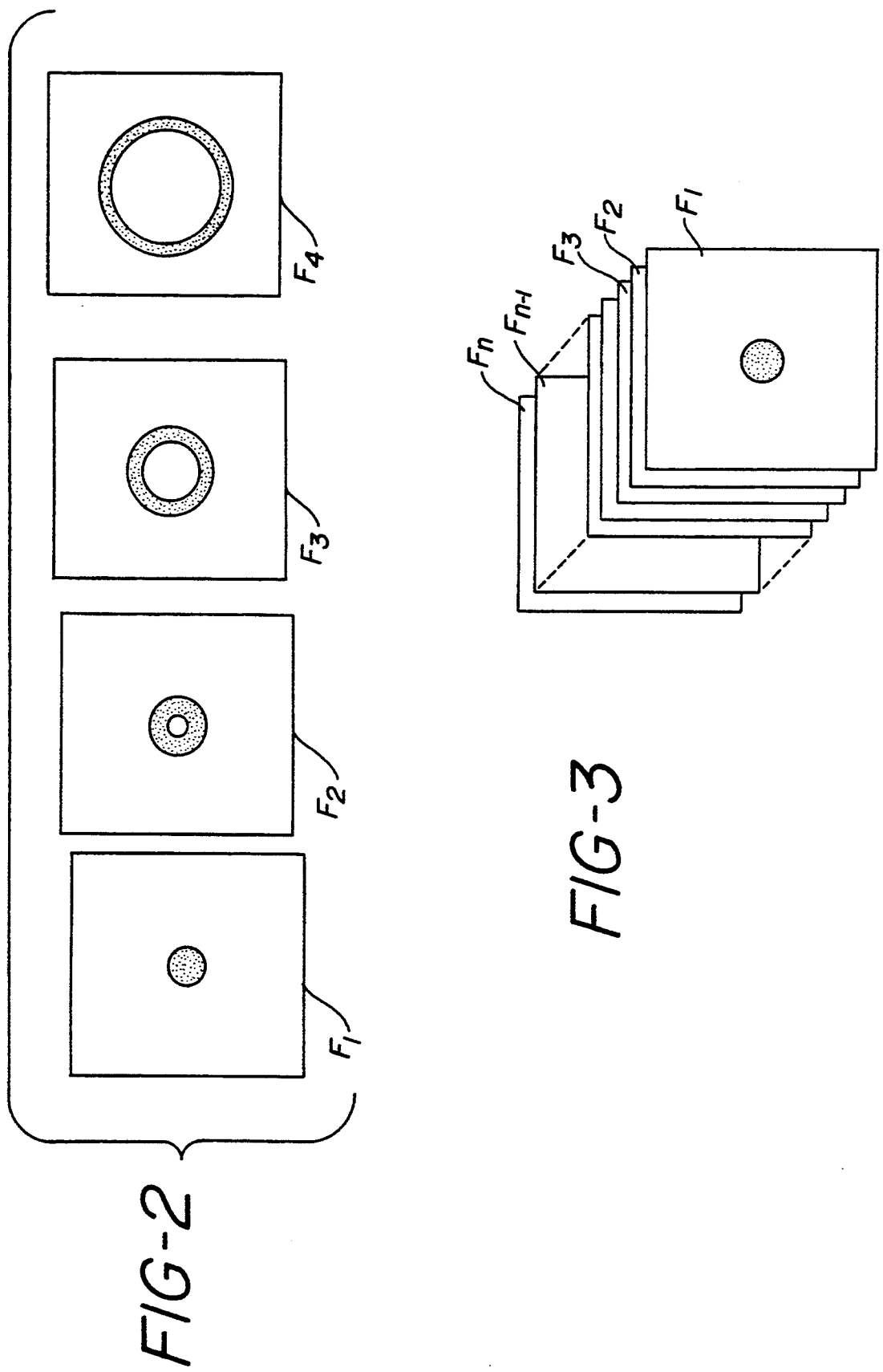

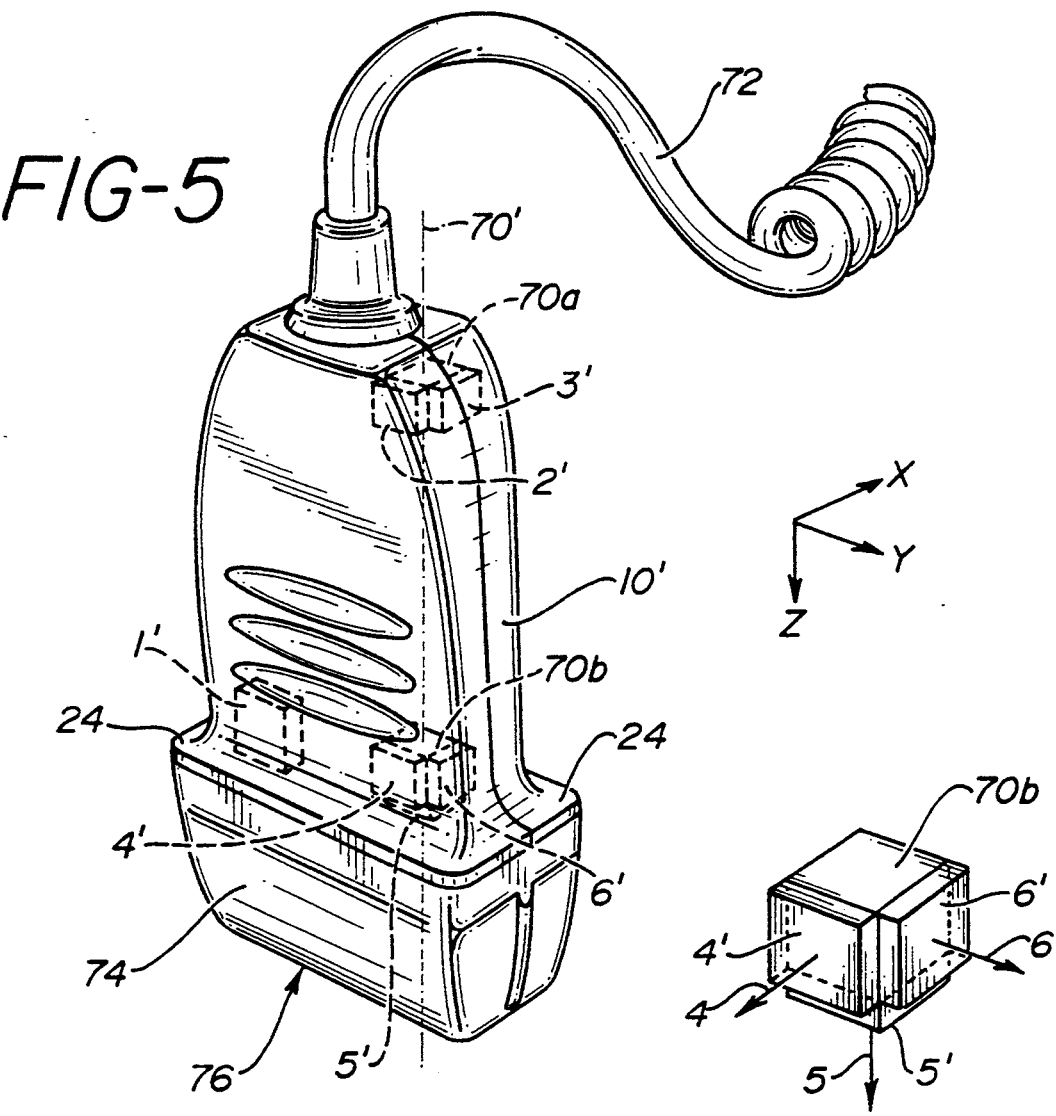

ACQUISITION AND DISPLAY OF ULTRASONIC IMAGES FROM SEQUENTIALLY ORIENTED IMAGE PLANES

This invention relates to the acquisition and display of ultrasonic images from sequential image planes of a subject, such as a spatially consecutive sequence of images from parallel image planes. This invention finds one of its applications in the presentation of two dimensional image information in a manner which gives the effect of three dimensions.

Two dimensional ultrasonic images are traditionally a collection of sequentially oriented individual lines taken over a planar region of a subject. This is because the ultrasonic scanhead which transmits and receives acoustic information is designed to "look" along only one line or vector at a time. The scanhead gathers information over a depth of field from a given direction, then through mechanical or electrical steering of the scanhead transducer the scanhead "looks" along a sequence of such vectors or directions in the image plane. The scan converter will then store and orient all of these image lines in their proper planar orientation, which is conventionally either parallel or radial. The assembly of all of the lines is the basis of a two dimensional image of the subject in the plane being scanned for display.

Such conventional two dimensional ultrasonic images depict image information in two directions. The direction along the length of each vector or line is depth into the object or patient being scanned. The second direction, from line to line, is a lateral direction which is approximately parallel to the scanning surface. In accordance with the present invention, a sequence of conventional two dimensional images are acquired and displayed in a second lateral direction from one conventional image plane to another. The display of two dimensional images in their sequential order in this second lateral direction results in an effective three dimensional presentation of the image information. One such effective presentation is made by displaying the sequence of images in rapid succession. The display of images may continuously show the images in the same sequence, or may display them cyclically from first to last, then last back to first. In accordance with one aspect of the present invention, a perception of depth in the second lateral direction or dimension is enhanced by displaying the content of a number of sequential images simultaneously, wherein contributions of individual image planes are weighted as a function of position in the sequence.

When acquiring ultrasonic image sequences for use in accordance with the foregoing or other techniques of three dimensional presentation, it is frequently useful or necessary to know the position of each image plane relative to the others. Such positional information allows the combined planes to be appropriately weighted, for instance, and is often needed to enable the graphical reconstruction of three dimensional surfaces within the subject being imaged. Attempts in the prior art to generate such positional information have usually been cumbersome, such as the articulating arm of prior art B-arm scanners, or have been restraining when employed in combination with the conventional hand-held scanhead. For instance one prior art technique generated repetitive sharp sounds from the scanhead by means of a spark gap. The sounds were detected by a number of audio detectors located around the scanhead and position determined by triangulation. It is accordingly desirable to be able to provide positional information about the image plane of the scanhead without interfering with the clinician's ability to use the scanhead in the conventional manner.

In accordance with a further aspect of the present invention positional information about the image plane of the scanhead is derived by incorporating a plurality of accelerometers as a part of the scanhead. The accelerometers generate electrical signals representative of acceleration along predetermined axes when the scanhead is moved. By integrating these acceleration values the relative coordinates of the scanhead can be determined in three dimensional space, then a transformation made to the orientation of the image plane extending from the scanhead.

In accordance with yet another aspect of the present invention positional information about the scanhead is derived by operating the scanhead within a three dimensional DC magnetic field. As each orientation of the DC field is generated about the scanhead, a magnetic flux is developed within a correspondingly oriented flux gate magnetometer which is a part of the scanhead. Each magnetometer thereby presents electrical signals which are functionally related to the relationship of the magnetometer to the corresponding magnetic field orientation, and this relational information is used to develop signals representative of the relative position and orientation of the scanhead's image plane.

In accordance with yet a further aspect of the present invention the ultrasonic image display provides a reference image to orient an acquisition sequence. With the reference image displayed on the screen, the relative orientation of the sequence of acquired images is shown by displaying the outline of the acquired images in perspective orientation, and also the line of intersection of each acquired image and the reference image if such intersection occurs, Such a display technique has been found to be effective in orienting the user to the spatial relationship of the acquisition sequence to the subject being scanned.

In the drawings

FIG. 1 illustrates in block diagram form an ultrasonic imaging system adapted to acquire a sequence of spatially related images;

FIG. 2 illustrates a sequence of spatially related images of a hollow ball;

FIG. 3 illustrates the ordering of the sequence of images of FIG. 2 for display in a three dimensional presentation;

FIG. 4 illustrates a scanhead axis about which a plurality of accelerometers are arrayed to produce signals for scanhead position determination;

FIG. 5 is a perspective view of a scanhead containing accelerometers for position determination;

FIG. 6 illustrates an arrangement for acquiring sequences of spatially related images in which the scanhead includes fluxgate magnetometers for sensing orientation in a magnetic field.

Figure 6:
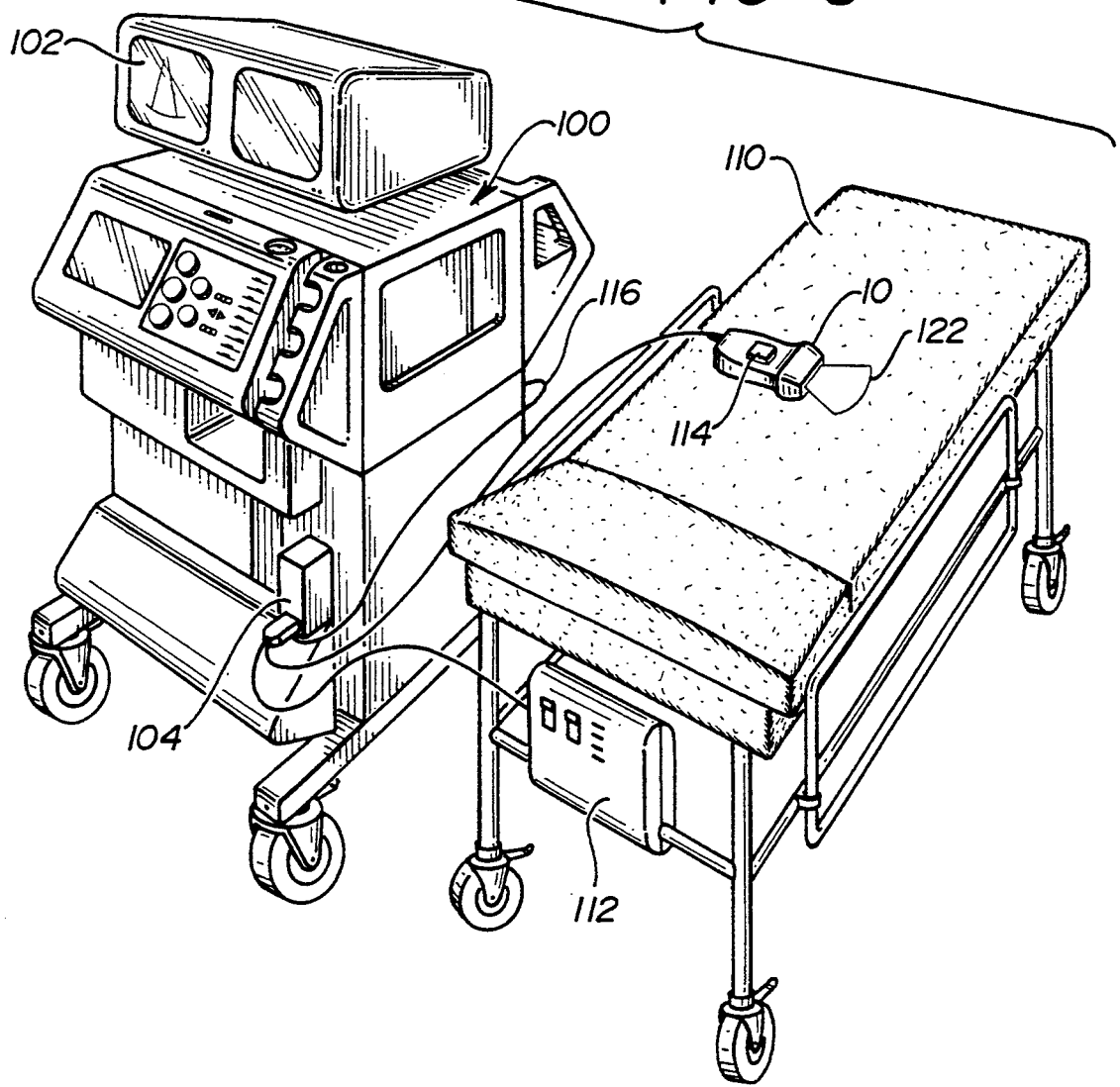
FIG. 6 is a detailed view of the mounting of accelerometers for the scanhead of FIG. 5.

A system for acquiring ultrasonic image information and presenting such image information in a three dimensional image format is shown in FIG. 1. A linear array scanhead 10 transmits pulses of ultrasonic energy and receives echoes returned from the subject being imaged.

The returning echoes are converted to electrical signals by the transducer array in the scanhead and applied to a beamformer 12, which combines the electrical signals to form a coherent vector of ultrasonic image information. The vector information is applied to a scan converter and memory 14, which forms an array of two dimensional image information which is displayed on a display 40. As the subject is being scanned and real-time images are appearing on the display, a particular image can be frozen on the screen by pressing the freeze button 16. If the user desires to save the frozen image, a save button 22 is pressed and the displayed image is stored in an image memory 20.

After a number of images are viewed and stored in the image memory 20 in this manner, the sequence of images may be reviewed by pressing a load button 36 to load the sequence of images saved by the image memory into a cineloop(R) frame store 30. The cineloop frame store has a capacity of 160 image frames, and retains the loaded images in an ordered sequence. By adjusting the sequence control 34 the user determines how the sequence of images is to be displayed: from first through last repetitively, from last to first repetitively, or sequencing from the first image to the last image, then back from the last to the first in a continuous loop. The rate control 32 enables the user to determine the rate at which the frames are displayed, from a slow rate to a fast rate. The cineloop frame store thus plays back the stored images in the desired sequence for review on the display 40.

As an example of the scanning techniques which may be performed by this arrangement, consider the scanning of a hollow ball, setting aside for the moment considerations of the ultrasonic transmission medium. The hollow ball is scanned by initially locating the scanhead to scan a plane which is adjacent to the ball. The scanhead is then moved normal to this plane in increments of 1 mm. At each incremental position an image of the plane being scanned is frozen on the display and stored in the image memory. The first image, acquired as the scan plane just begins to intersect the edge of the ball, is shown as frame $F_1$ in FIG. 2. At the next incremental position of the scanhead a cross-sectional image as shown in frame $F_2$ is acquired and saved. Subsequent increments in the position of the scanhead and the scan plane produce further "slices" of the ball, as shown by frames $F_3$ and $F_4$ in FIG. 2.

This scanning and image acquisition process continues until the scan plane passes the opposite side of the ball. The sequence of two dimensional images thereby acquired and stored in the image memory is shown in FIG. 3, beginning with image frame F1 and continuing through the last frame $F_n$. The sequence of images is then loaded into the cineloop frame store 30. The display sequence 34 and rate 32 adjustments are set for the desired display rate and sequence and the sequence of images is played back on the display 40. When these sequential, parallel oriented images are played back on the display, the viewer is given a three-dimensional presentation of the hollow ball.

In accordance with the principles of the present invention the three-dimensional appearance of the image sequence may be enhanced by weighting the image content of the frames. A preferred weighting technique is to give greater weight to the frames which are in front, that is, image slices which are closer to the viewer, than frames which are in the rear. This presents the near field of the three dimensional object more strongly than the the image frames of the far field, where near and far refer to the sequential direction. The progressive weighting from the front of the object to the back may be scaled linearly or exponentially depending upon the desired effect.

The weighted frames may be viewed in several different ways. One way is to play the sequence of weighted frames in rapid succession. This would present the sequence in a "swim through" mode or a "swim back and forth" mode as described in U.S. Pat. No. 4,297,009. A second way is to stack, or overlay the weighted frames into a single composite frame. A third way is to perform a corresponding pixel-by-pixel summation process of the weighted frames, then divide the result by the number of images in the sequence. An effective implementation of the second technique is to weight the last frame, frame $F_n$ in FIG. 3, by 40%, and the next adjacent frame $F_{n-1}$ by 60%. The two weighted frames are combined into a composite frame, 40% of which is contributed by the most distant frame and 60% of which is contributed by the next adjacent frame. This composite frame is then weighted by 40% and the next adjacent frame $F_{n-2}$ is weighted by 60%. The weighted composite frame and the weighted frame $F_{n-2}$ are combined to form a new composite frame. This weighting and combining process is continued, progressing to the nearest frame $F_1$, resulting in a final composite frame with the near field more greatly weighted than the far field. It may be appreciated that the weighting progression may be made as liner or nonlinear as desired; for example, a constant weighting of 50% to each of N frames and their composite would result in a progressive weighting function that would be expressed as $(0.5)N$. It has been found that at a net weighting of 5% the content of an image makes no appreciable contribution to the composite image. Hence, an effective presentation has been made by deleting up to one-third of the far field frames, then progressively weighting the remaining two-thirds of the frames from the far to the near field.

A number of mechanisms have been devised and proposed to provide the positional information of ultrasonic image planes. For instance, the well-known B-arm scanning system with a linear array transducer connected at the end of the articulating B-arm with potentiometer resolvers at the joints could be used to acquire a sequence of substantially parallel image frames. However, the sequence of images need not be parallel to present the three-dimensional effect. For instance, the scanhead could be rocked to acquire a sequence of images at sequential angular increments, or the scanhead could be rotated about the center of the face to acquire a sequence of image planes which pass through a common axis.

The B-arm mechanism however is sizeable, often awkward, and lacks the portability and ease of use of current hand-held scanheads. Accordingly it would be preferable to provide a means for position determination in a hand-held scanhead. One such preferred device for acquiring a sequence of images at known positional increments is illustrated in FIGS. 4 and 5. The bar 70 in FIG. 4 represents a central axis of a scanhead, such as a horizontal axis 70' of scanhead 10' of FIG. 5. Located inside the scanhead case 24 and oriented as indicated by acceleration vector arrows 1-6 in FIG. 4 are six accelerometers. A preferred accelerometer is type AMD-CK/0A2, available from Access Sensors SA. These accelerometers are capable of resolving very small acceleration forces, down to one milliGravity (mG). Six of these accelerometers positioned as indicated in FIG. 4, with 5 parallel to the axis, 4 and 6 normal to 5 and to each other, 2 and 3 at the other end of the axis and parallel to 4 and 6, and 1 offset from and parallel to 4, enable the resolution of any change in orientation of the scanhead, be it a change in cartesian coordinates x, y, and z, or a rotational change in roll, pitch, or yaw. The acceleration signals produced by the six scanhead accelerometers are applied by means of the scanhead cable 72 to an increment calculator 80 in the system processor as shown in FIG. 1.

In the construction of a scanhead the axis 70' passes through the centers of two rigid bodies such as aluminum cubes 70a and 70b. The aluminum cubes are mounted inside the scanhead case 24. The lower portion 74 of the scanhead houses the ultrasonic transducer, which transmits and receives ultrasonic energy through an acoustic window 76. Attached to certain faces of the aluminum cubes 70a and 70b are accelerometers 2', 3', 4', 5', and 6', which detect acceleration in directions corresponding to the respective unprimed numbered vectors of FIG. 4. An enlarged view of cube 70b is shown in FIG. 5a, with its attached accelerometers 4', 5', and 6'. As this FIG. 5a indicates, the three vectors 4, 5, and 6 all coincide at the center of the cube. Wires (not shown) from the individual accelerometers lead to the scanhead cable 72 and the increment calculator 80. FIG. 5 also shows that the accelerometer 1' is spaced apart from the aluminum cubes and their axis 70' inside the scanhead, where the separate accelerometer 1' is in an orientation to sense rotation about the axis 70'.

Positional information of the scanhead is computed from the six acceleration signals as follows. The signals from the accelerometers is continuously sampled at a predetermined sampling rate and analyzed. Since the acceleration signals provide relational data and the position of the scanhead is arbitrarily determined by the user, some reference must be established for the positional information. This is accomplished by initializing the position of the scanhead when it is at rest. When the scanhead is at rest the only acceleration force being experienced by the accelerometers is gravitational acceleration. Hence the increment calculator will check for initialization by verifying that the accelerations remain constant and that the magnitude of the acceleration vector is equal to gravitational acceleration (9.8 m/sec$^2$). At the starting rest position the x,y,z coordinate system of the scanhead is established as the origin point for all subsequent calculations.

As the scanhead is moved during scanning to acquire a sequences of ultrasonic images, the accelerometers experience acceleration forces and their output signals are continually sampled to produce a continuous stream of position data. The output signals are combined in the following manner to determine linear and angular acceleration characteristics of the scanhead and correspondingly of the image plane:

$$d^2x/dt^2 = -a_4 - g_x$$

$$d^2y/dt^2 = a_6 - g_y$$

$$d^2z/dt^2 = a_5 - g_z$$

and $$d^2roll/dt^2 = (a_3 - a_6)/D_1$$

$$d^2pitch/dt^2 = (a_2 - a_4)/D_1$$

$$d^2yaw/dt^2 = (-a_1 + a_4)/D_2$$

where X, Y, and Z are taken in relation to the coordinates shown adjacent FIGS. 5 and 5a; $D_1$ is the distance between the centers of the two aluminum cubes 70a and 70b; $D_2$ is the distance between the center of accelerometer 1' and the center of cube 70b; the "a" terms are acceleration values of the accelerometers of FIGS. 5 and 5a in correspondence to the subscript numerals; and gx, gy, and gz are the three vector components of gravitational acceleration. As the second differential notation of the three expressions indicates, the second integral of these expressions taken as a function of the signal sampling rate (time) will yield the three translational and rotational characteristics of position in relation to the starting rest position.

The scanhead of FIG. 5 with the accelerometer position determination arrangement is used to acquire a sequence of image frames for three-dimensional presentation in the following manner, with reference to FIG. 1. The user first adjusts the Set Increment control 82 on the imaging system to determine the increments at which images in the sequence are to be acquired. The increments could be every 1 mm for linear movement of the scanhead, or every 10° for rotational movement of the scanhead, or every n milliseconds, for instance. The user then positions the scanhead at its starting rest position. The user presses the Initialization button 84 to cause the system to initialize position as discussed above. Increments then proceed from this initial position. The user then proceeds to scan by moving the scanhead in the desired manner. The movement of the scanhead is detected by the accelerometers and acceleration is resolved to position. As the desired positional or time increments are attained as determined by the Increment Calculator 80, the Save button 22 is automatically triggered to save an image frame at each increment. When the scanhead comes to a stop the sequence acquisition is terminated unless acquisition is manually terminated by the user. The image memory now contains a sequence of images obtained at the desired increments, which may then be displayed as desired in a three-dimensional presentation.

A second preferred device for acquiring a sequence of images at known positional increments is illustrated in FIG. 6. This arrangement operates by detecting the location of the scanhead 10' in an electromagnetic field. In considering this principle of position detection a number of factors will affect the complexity and ease of use of such a system. An arrangement which requires multiple transmitters or receivers, such as an r.f. triangulation system or time of flight or phase differential system, would be undesirable by reason of the multiplicity and complexity of hardware. The arrangement must also be relatively impervious to the presence of metallized components frequently found in hospitals and to the electronic components of ultrasonic imaging equipment. Any arrangment must also be precise enough to resolve to millimeter sized increments.

Consideration of these factors led to the desirability of a magnetic field locational technique such as that described in U.S. Pat. Nos. 4,945,305 and 4,849,692. Such an arrangement advantageously requires only one transmitter and one receiver due to the polarization of the transmitted magnetic field. The use of a D.C. field makes this technique relatively immune to the electronics of an ultrasonic imaging system as well as to eddy currents induced in nearby metallic components such as hospital bedframes. Such systems also are capable of the resolution required for three dimensional image sequence acquisition.

Referring to FIG. 6, an ultrasonic imaging system 100 is shown with a dual monitor display 102. Adjacent to the imaging system 100 is a hospital bed or gurney 110 on which a patient may recline during ultrasonic scanning. Both the imaging system 100 and the hospital bed 110 are portable for ease of use as indicated by the wheels on both elements. Attached to a lower crossbar of the hospital bed frame is a transmitter 112, which transmits a magnetic field in pulsed bursts of different spatial polarities. On the hospital bed is a scanhead 10 to which is attached a magnetic field receiver 114 which includes a plurality of magnetometers. Cables from the scanhead, magnetic field receiver, and the transmitter are commonly connected to a scanhead input port 104 of the imaging system 100 so that all components of the system are operated under common control. A fourth cable 116 leads to a user operated footpedal (not shown) which is advantageously used as described below. The pulsed magnetic field transmitter and magnetic field receiver components are available from Ascension Technology Corporation of Burlington, Vt. USA.

In operation the transmitter 112 transmits a magnetic field which is spatially oriented with respect to the position of the transmitter. The magnetic field and its orientation are sensed by the receiver 114. The receiver 114 produces a matrix of digital signals which describe translational and rotational characteristics in homogeneous coordinates of the location of the receiver, referenced to the transmitter location and position. These signals, which are transmitted by cable to the imaging system, are of the form $$\begin{bmatrix} R_{3\times 3} & \begin{matrix} 0 \\ 0 \\ 0 \end{matrix} \\ \hline T_{1\times 3} & 1 \end{bmatrix}$$

where $R_{3\times 3}$ is a three by three submatrix of rotational data and $T_{1\times 3}$ is a one by three submatrix of translational data.

Figure 7:
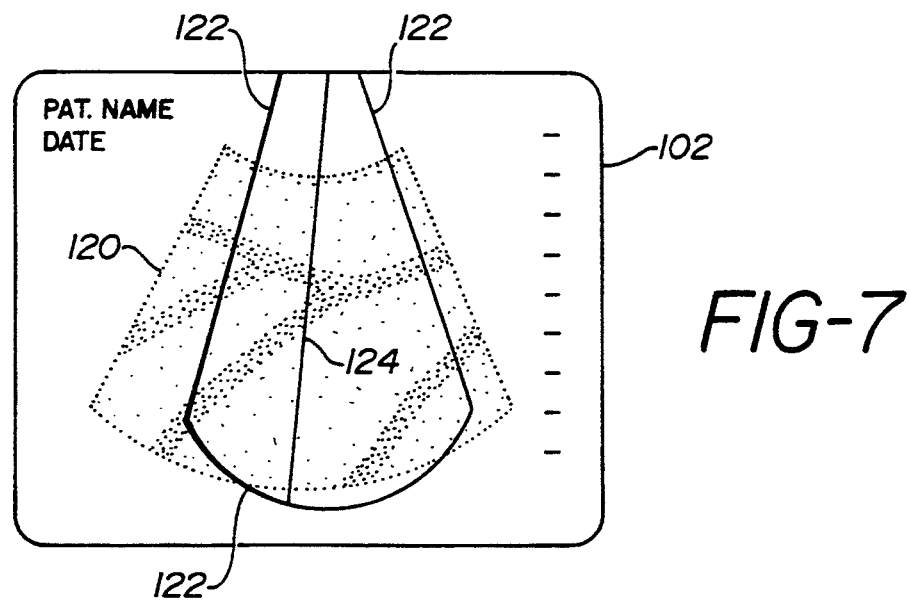
FIG. 7 illustrates the reference and real time image display of the arrangement of FIG. 6.

This positional information is used to create a display as shown in FIG. 7, which has been found to be especially useful during the acquisition of sequences of spatially related images. The user manipulates the imaging system in the following manner to produce this display. Initially the user is surveying the anatomy of the patient, producing real time images on the display 102 as indicated by the arcuate, trapezoidal image sector 120. (In a particular application the sector shape is determined by the characteristics of the scanhead, and may be rectangular, trapezoidal, or some other shape.) When the user locates a desirable reference image plane, the user depresses the footpedal, which freezes the reference image 120 on the display. The acquisition of the sequence of spatially related images is taken with reference to this plane, which may desirably show characteristic anatomy or other physical landmarks which are to be the subject of the imaging sequence.

With the reference plane image frozen on the display, the user manipulates the scanhead to the starting location from which the image sequence is to be acquired. As the scanhead is manipulated, the display produces an outline of the image sector on the display in a perspective view which conveys the orientation of the image sector in relation to the reference image plane. Additionally, the display shows a line 124 where the plane of the image sector 122 intersects the plane of the reference image 120, if such intersection occurs. Thus, as the user manipulates the scanhead, the display continuously shows the relation of the image sector 122 to the reference as the sequence of spatially related images is acquired.

A typical acquisition scan would comprise orienting the image sector at approximately a 90° angle to the reference image and at the left of the image, then sweeping the scanhead from left to right while holding the 90° orientation. As the scanhead is swept, the consecutively acquired images and their associated locational information are stored in a cineloop image memory. A preferable operating technique is to allow the cineloop memory to run continuously, then to stop it when the acquisition sequence is completed. The cineloop memory will then retain the last n images of the sequence, where n is the cineloop memory capacity. Preferably the image and positional information is stored in a "tagged" format, where each block of image data is accompanied by a data tag that stores the positional information. The sequence of images with its positional information is then conveniently available for subsequent processing, analysis, or three dimensional display.

The outline 122 of the real time image sector is continuously computed and displayed in the following manner. For any point of the real time sector there is a corresponding point on the display where the point of the sector is to be displayed to be in proper perspective with the plane of the reference image. In particular, the real time sector points to be displayed are those that are predefined as the maximum depth locations (arcuate portion) and the lateral sides of the image sector, which outline the sector. To transform any sector outline point to a point on the display a number of coordinate system transformations are required. Consider first that the outline 122 of the sector which is spatially located at the front of the scanhead 10 as shown in FIG. 6 bears a constant relationship to the receiver 114 attached to the scanhead. A first transformation is needed to transform the sector coordinates in space to the coordinate system of the receiver. Next a transformation is needed from the coordinates of the receiver 114 to the coordinates of the transmitter 112, which provide the spatial origin point. Then a transformation is needed from the transmitter 112 to the coordinates of the receiver 114 at the time the reference image was acquired, which do not change after acquisition of the reference image. Then an unchanging transformation from those receiver coordinates to the reference image sector in front of the scanhead is required. Finally, an unchanging transformation is needed from the reference image sector to the pixels on the display.

These transformations can also be described mathematically by a number of transformation matrices. One is a matrix $M_D$, which translates the coordinates of any point x on the sector outline to the coordinates of the receiver 114 on the scanhead. A second transformation matrix M translates the coordinates of the receiver 114 to the absolute spatial coordinates defined by the location of the transmitter 112. A third transformation matrix is matrix $M_S$, which translates the coordinates of the sector to pixel locations on the display 102. A final matrix $M_o$ is defined when the footpedal is depressed, and is the matrix representing the coordinates of the receiver 114 when the reference plane is determined and displayed. From these transformation matrices the display locations x' of each point on the sector outline 122 is computed by $$x'=x(M_DM)(M_DM_o)^{-1}(M_s)$$

The intersecting line 124 of the reference image and the real time sector is computed by defining the z coordinate of the reference plane as $z=0$, then examining points on the sector outline for which $z=0$. The arcuate portion of the real time sector outline 122 is extended to form an imaginary, full 360° circle and a second point on the imaginary circle for which $z=0$ is located. The line 124 is then formed by connecting these two points of planar intersection within the boundary of the sector outline 122.

In order to further enhance the visualization of depth for the real time sector outline, that portion of the real time sector which is in front of the reference plane is displayed with greater enhancement than the portion which is behind the reference plane. For example the forward portion of the sector or its outline could be displayed with greater brightness than the portion which is behind the image plane.

Further variations of the foregoing will readily occur to those skilled in the art. For instance, the inverse of the display of FIG. 7 may be generated. That is, the real time image is displayed in the display plane, overlaid by the projection of the outline of the reference image. This variation advantageously shows not just the outline of the real time sector, but also the image information thereof in a single display. Another variation would be to display the real time image in the display plane, and an oblique projection of the outlines of two rectangles of the reference and real time image planes. This latter approach may provide easier comprehension of the geometric relationship of the two planes. As an alternative to the brightness differentiation of the forward and rearward sector portions discussed above, variation of the line width as a function of proximity to the viewer could accomplish the same purpose.

What is claimed is:

1. An ultrasonic imaging system for providing planar image information, said system including means for providing spatially identified planar images comprising:
   a scanhead including means for ultrasonically scanning a plane of a subject;
   means connected to said scanhead for determining the spatial location of said plane; and
   display means connected to said scanhead and said determining means for displaying reference plane information and real time image plane information in an orientationally relational projection to each other,
   wherein the information of one of said planes contains information concerning the structure of said subject and the information of the other of said planes comprises the outline of an image plane.

2. The ultrasonic imaging system of claim 1, wherein said outline is displayed in a manner depicting depth.

3. The ultrasonic imaging system of claim 1, wherein the brightness or the width of said outline is varied in said display as a function of depth.

4. The ultrasonic imaging system of claim 1, wherein said image plane outline further includes a line indicating the intersection of said two planes.

* * * * *